United States Patent
Li et al.

(10) Patent No.: US 9,725,650 B2
(45) Date of Patent: Aug. 8, 2017

(54) REACTIVE MONOMER, A LIQUID CRYSTAL PANEL AND AN ELECTRONIC EQUIPMENT

(71) Applicant: Shenzhen China Star Optoelectronics Technology Co., Ltd., Shenzhen, Guangdong (CN)

(72) Inventors: Xiang Li, Guangdong (CN); Yanjun Song, Guangdong (CN); Chung-ching Hsieh, Guangdong (CN)

(73) Assignee: Shenzhen China Star Optoelectronics Technology Co., Ltd, Shenzhen, Guangdong (CN)

( * ) Notice: Subject to any disclaimer, the term of this patent is extended or adjusted under 35 U.S.C. 154(b) by 226 days.

(21) Appl. No.: 14/433,674

(22) PCT Filed: Dec. 4, 2014

(86) PCT No.: PCT/CN2014/093017
§ 371 (c)(1),
(2) Date: Apr. 5, 2015

(87) PCT Pub. No.: WO2016/078159
PCT Pub. Date: May 26, 2016

(65) Prior Publication Data
US 2016/0340583 A1   Nov. 24, 2016

(30) Foreign Application Priority Data

Nov. 21, 2014 (CN) .......................... 2014 1 0677453

(51) Int. Cl.
| | | |
|---|---|---|
| *G02F 1/1333* | (2006.01) | |
| *C09K 19/12* | (2006.01) | |
| *C07C 69/54* | (2006.01) | |
| *G02F 1/1337* | (2006.01) | |
| *C07C 69/653* | (2006.01) | |
| *G02F 1/1335* | (2006.01) | |
| *G02F 1/1368* | (2006.01) | |
| *C09K 19/38* | (2006.01) | |
| *C09K 19/04* | (2006.01) | |

(52) U.S. Cl.
CPC .............. *C09K 19/12* (2013.01); *C07C 69/54* (2013.01); *C07C 69/653* (2013.01); *C09K 19/3804* (2013.01); *G02F 1/1337* (2013.01); *G02F 1/1368* (2013.01); *G02F 1/133365* (2013.01); *G02F 1/133514* (2013.01); *C09K 2019/0448* (2013.01); *C09K 2019/123* (2013.01); *G02F 2001/133302* (2013.01); *G02F 2001/133742* (2013.01); *G02F 2202/022* (2013.01)

(58) Field of Classification Search
CPC ................ C09K 19/12; C09K 19/3804; C09K 2019/123; C09K 2019/0448; C07C 69/54; C07C 69/653; G02F 1/1333; G02F 1/133365; G02F 1/133514; G02F 1/1368; G02F 1/1337; G02F 2001/133302; G02F 2001/133742; G02F 2202/022
USPC ..... 252/299.01, 299.6, 299.66; 349/182, 183
See application file for complete search history.

(56) References Cited

U.S. PATENT DOCUMENTS

| | | | |
|---|---|---|---|
| 2012/0292568 A1 | 11/2012 | Kuriyama et al. | |
| 2012/0292569 A1 | 11/2012 | Kuriyama et al. | |
| 2014/0132899 A1* | 5/2014 | Hsieh ..................... | C09K 19/56 349/106 |

FOREIGN PATENT DOCUMENTS

| | | |
|---|---|---|
| CN | 101671252 A | 3/2010 |
| CN | 102851037 A | 1/2013 |
| CN | 102964253 A | 3/2013 |
| CN | 103666481 A | 3/2014 |

* cited by examiner

*Primary Examiner* — Geraldina Visconti
(74) *Attorney, Agent, or Firm* — Andrew C. Cheng

(57) ABSTRACT

The invention discloses a reactive monomer, a liquid crystal panel and an electronic equipment. The reactive monomer comprises a biphenyl structure and polymeriable groups connecting at both sides of the biphenyl structure, a structure of the reactive monomer is

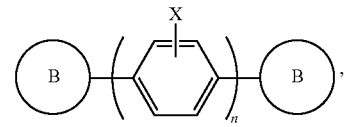

wherein, n≥3 B are the polymerizable groups;
the liquid crystal panel in the invention comprises both a first substrate and a second substrate with disposed alignment films respectively, and a liquid crystal layer disposed between the first substrate and the second substrate, and the liquid crystal layer comprises the liquid crystal compound which comprises the reactive monomer. The reactive monomer in the invention can absorb ultra violet light more efficiently, shorten an illuminating time of UV1, and increase production efficiency.

7 Claims, 5 Drawing Sheets

REACTIVE MONOMER, A LIQUID CRYSTAL PANEL AND AN ELECTRONIC EQUIPMENT

FIELD OF THE INVENTION

The invention relates to an optical material technology field, particularly to a reactive monomer, and both a liquid crystal panel and an electronic equipment with the reactive monomer.

BACKGROUND OF THE INVENTION

PSVA (Polymer stabilized vertical alignment) technology is a stable vertical alignment technology of polymer, and the biggest feature herein is utilizing VA liquid crystal to form a pretilt angle of polymer layer on a alignment film 1 (PI).

The concrete forming process comprises four steps as shown in FIG. 1, (1): adding a certain ratio of polymerizable reactive monomer 2 (RM, Reactive monomer) in a liquid crystal medium, and the reactive monomer 2 is polymerized into macromolecule network after illuminated by ultra violet light; (2) before illuminating by UV light 4, adding a voltage between up-substrate 51 and down-substrate 52 to form a liquid crystal molecule 3 a pretilt angel; (3) illuminating by particular UV light 4 after stabilizing the voltage to make reactive monomer 2 to polymerize macromolecule network, and the reactive monomer 2 moves to a surface of the alignment film 1 to anchoring the liquid crystal molecule 3 on the surface; (4) after turning off the voltage, the liquid crystal molecule 3 is formed into a certain pretilt angle because of anchoring polymer and not able to get back to the initial position. The pretilt angle is used to increase an effective time of liquid crystal, and the process of UV light 4 illuminating is UV1.

In PSVA technology, mainly by controlling illumination time of UV1 to control the pretilt angel of liquid crystal and then further control the optical properties of liquid crystal panel. However, an effect of productivity decreases because the illumination time of the UV1 is too long.

SUMMARY

A technical problem mainly to be solved in the invention is to provide a reactive monomer, a liquid crystal panel and an electronic equipment to shorten illuminating time of UV1 and then increase productivity efficiency.

To solve the aforementioned technical problem, a technology program applied in the invention is: to provide a reactive monomer, which comprises a biphenyl structure and polymeriable groups connecting at both sides of the biphenyl structure, a formula I of the reactive monomer is shown as:

fomular I

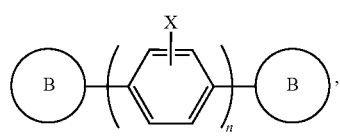

wherein, n≥3; B are the polymerizable groups.

Wherein, the polymerizable groups are acrylic ester or methacrylate.

Wherein, a formula of the reactive monomer is shown as formula II:

fomula II

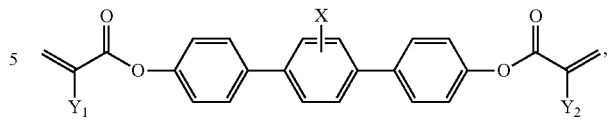

wherein, the X is one selected from —H, —F, —CF$_3$ or —CH$_3$; the Y$_1$ and Y$_2$ groups are respectively selected from one of —H or —CH$_3$.

In order to solve the aforementioned technical problem, another technology program applied in the invention is: to provide a liquid crystal composition which comprises at least one of the reactive monomer.

In order to solve the aforementioned technical problem, another technology program applied in the invention is: to provide a liquid crystal panel comprising both a first substrate and a second substrate with disposed alignment films respectively, and a liquid crystal layer disposed between the first substrate and the second substrate, and the liquid crystal layer comprises the liquid crystal compound.

Wherein, the first substrate is a color filter substrate; the second substrate is a thin film transistor array substrate; a side of the thin film transistor array substrate further disposes a layer of both tetrafluoroethylene and Polyfluoroalkoxy resin film.

Wherein, the alignment film is a vertical alignment film.

In order to solve the aforementioned technical problem, another technology program applied in the invention is: to provide an electronic equipment, which comprises a liquid crystal panel, and the liquid crystal panel comprises both a first substrate and a second substrate with disposed alignment films respectively, and a liquid crystal layer disposed between a first substrate and a second substrate, and the liquid crystal layer comprises a liquid crystal compound which comprises the aforementioned reactive monomer.

Wherein, the first substrate is a color filter substrate; the second substrate is a thin film transistor array substrate; a side of the thin film transistor array substrate further disposes a layer of both tetrafluoroethylene and Polyfluoroalkoxy resin film.

Wherein, the alignment film is a vertical alignment film.

The advantageous effects of the invention are: the situation is different from the prior art, that by utilizing the reactive monomer with plentiful biphenyl structures which is even more sensitive to ultra violet light so that absorbing ultra violet light more effectively, and energy inside molecule can be passed to the polymerizable groups at both sides after absorbing the ultra violet light to accelerate polymerization of the reactive monomer and to get a better reaction rate, so that shortening illumination time during manufacturing and increasing production efficiency.

Figure 1:
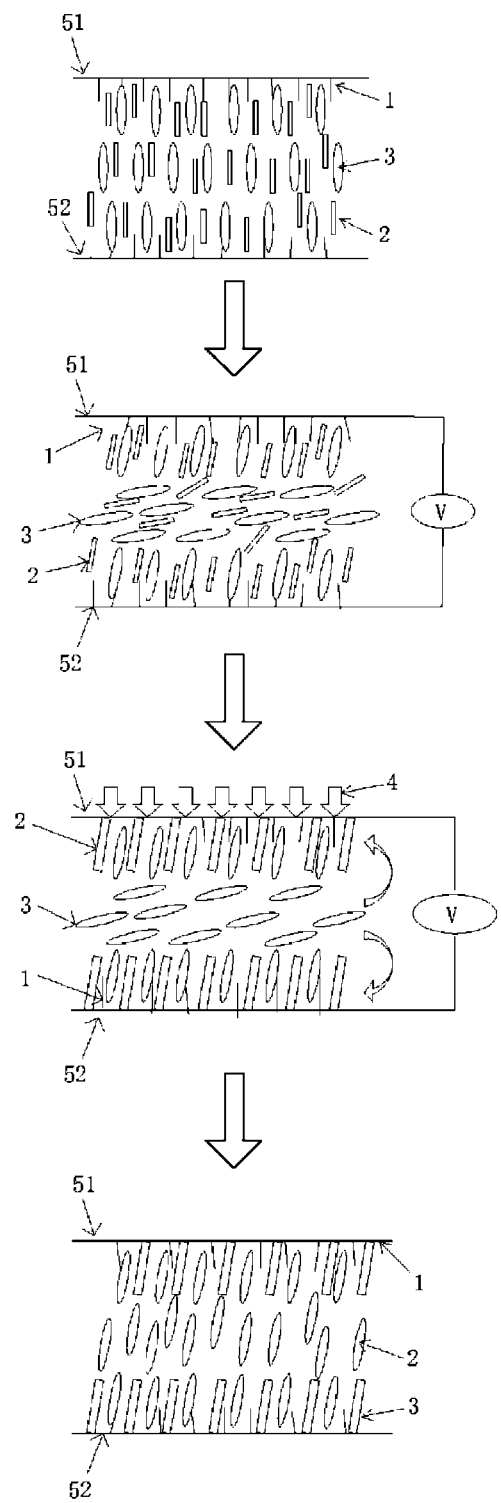
FIG. 1 is a flowchart schematic view of PSVA technical implementation of the background technology.

Wherein,
alignment film 1, 104
reactive monomer 2
liquid crystal molecule 3
UV light 4
up substrate 51
down substrate 52
first substrate 101
second substrate 102
liquid crystal layer 103

DETAILED DESCRIPTION OF THE EMBODIMENTS

Figure 2:
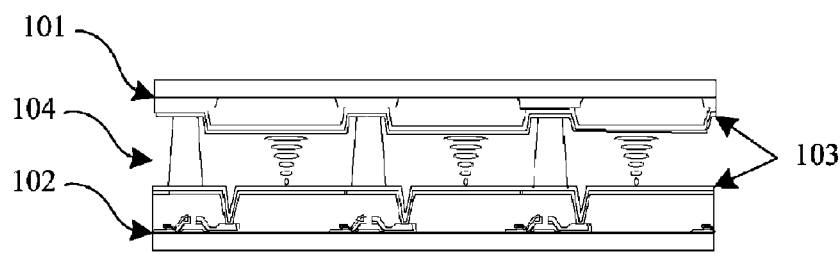
FIG. 2 is a structural schematic view of an implementation plan of a liquid crystal panel in the invention.

Please refer to FIG. 2, FIG. 2 is a structural schematic view of an implementation plan of a liquid crystal panel in the invention.

The liquid crystal panel comprises a first substrate 101, a second substrate 102 and a liquid crystal layer 104 disposed between the first substrate 101 and the second substrate 102, and the liquid crystal layer 104 comprises a liquid crystal compound which comprises a reactive monomer (hereinafter referred to as RM/B).

Both corresponding sides of the first substrate 101 and the second substrate 102 dispose alignment films 3 respectively. In this embodiment, the first substrate 101 is a color filter substrate (CF), the second substrate is a thin film transistor array substrate (TFT), and the alignment film 103 is a vertical alignment film. RM/B of the liquid crystal compound of the liquid crystal layer 104 comprises a biphenyl structure and polymeriable groups connecting at both sides of the biphenyl structure, a formula I of the reactive monomer is shown as:

fomular I

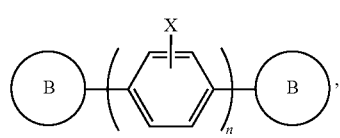

wherein, n≥3; B are the polymerizable groups which are acrylic ester or methacrylate.

In prior art, most of the reactive monomer (hereinafter referred to as RM/A) of the liquid crystal compound is single phenyl structure, but the RM/B in the implementation plan of the liquid crystal panel in the invention comprises plentiful phenyl structures that is more sensitive to ultra violet light so that absorbing ultra violet light more effectively, and energy inside molecule can be passed to the polymerizable groups at both sides after absorbing the ultra violet light to accelerate polymerization of the RM/B and to get a better reaction rate, so that shortening UV1 time and increasing production efficiency.

In the invention, number of n is 3≤n≤5, ex: n is equal to 3. When n is 3 and the polymerizable groups are acrylic ester or methacrylate, an absorbing wavelength of RM/B structure and a wavelength illuminating in UV1 are optimum matching, and the illuminating wavelength of UV1 in manufacturing is 250 nm-400 nm, or is 275 nm-350 nm, ex: 300 nm. So that the optical reaction efficiency is the best. Of course, n can be a number larger than 5 to match other wavelength. In this embodiment, a formula of the RM/B is further shown as formula II:

fomula II

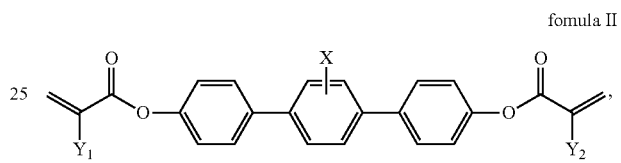

wherein, the X is one selected from of —H, —F, —CF$_3$ or —CH$_3$; the Y$_1$ and Y$_2$ groups are respectively selective from one of —H or —CH$_3$. For example, when X is —H, Y$_1$ is one of H or —CH$_3$, and Y$_2$ is also one of —H or —CH$_3$. When X is —F, Y$_1$ is one of —H or —CH$_3$, and Y$_2$ is also one of —H or —CH$_3$. When X is —CF$_3$, Y$_1$ is one of —H or —CH$_3$, and Y$_2$ is also one of —H or —CH$_3$. When X is —CH$_3$, Y$_1$ is one of —H or —CH$_3$, and Y$_2$ is also one of —H or —CH$_3$.

The synthetic route of RM/B is listed as following:

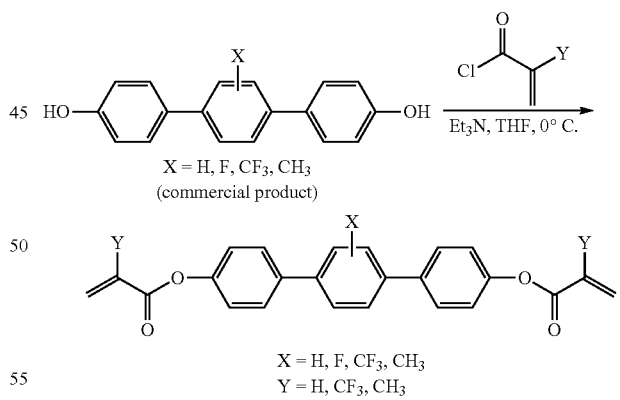

The manufacturing method of RM/B is as following: disposing 4.14 mmol initial compounds (commercialize) into a 250 ml two-neck bottle and after three times of pumping by a vacuuming deaerator and water-removal equipment and filling with nitrogen, connecting with nitrogen gas by a dropping tube to keep the reaction system in anaerobic and anhydrous situation. Adding 8.28 mmol Et$_3$N and 50 ml anhydrous THF at room temperature, and then stirring until dissolved. Then, adding an agent of 9.11 mmol Acryloyl chloride in cold water and then keeping the reaction at room temperature until the next day. Air exhausting and filtering by THF, collecting filterate into decompression and condensation, extracted by EA and water, removing water by MgSO$_4$ and then air exhausting and filtering, and then condensing vacuum to gain a yellow solid body. Finally, the target product is a light yellow solid body which can be purified by silica gel column chromatography with EA/Hexane=1:6. Of course, the target product can be recrystallized by tetrahydrofuran/methanol (THF/methanol).

Figure 4:
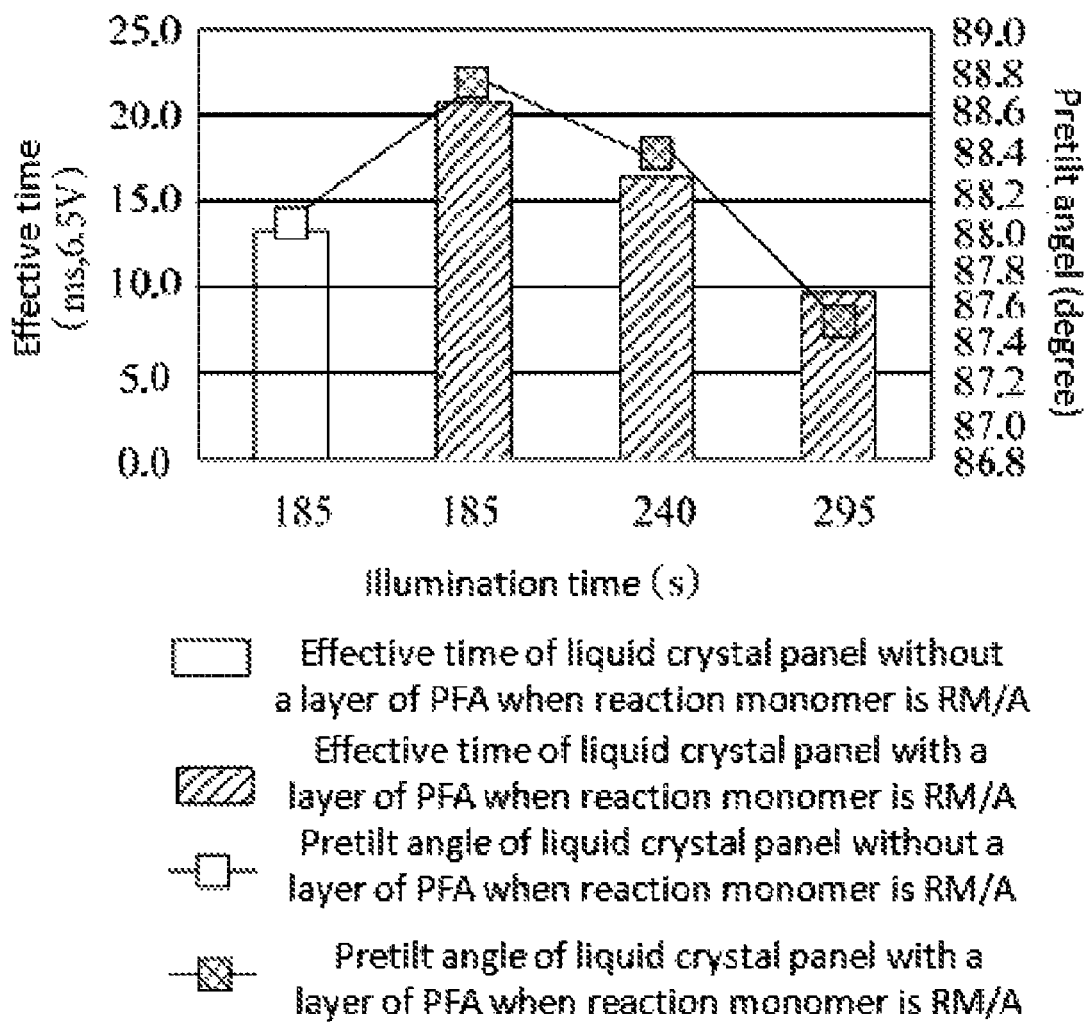
FIG. 4 is an effective time and pretilt angel schematic diagram representing a liquid crystal panel without a layer of PFA film at illumination time of 185 s in the prior art, and an effective time and pretilt angel schematic diagram representing a liquid crystal panel with a layer of PFA film in the prior art.

The RM/B starts a process of polymerization as following:

As shown in FIG. 4, after adding the layer of PFA and at illumination time of 185 s, an effective time of an liquid crystal panel increases a lot, and so do a pretilt angel. The illumination time takes longer to reach an efficiency without the layer of PFA.

Table 1 represents when a reactive monomer is RM/A, experimental data of an effective time and pretilt angel of a liquid crystal panel with a layer of PFA at different illumination times and data of a liquid crystal panel without a layer of PFA at illumination time of 185 s.

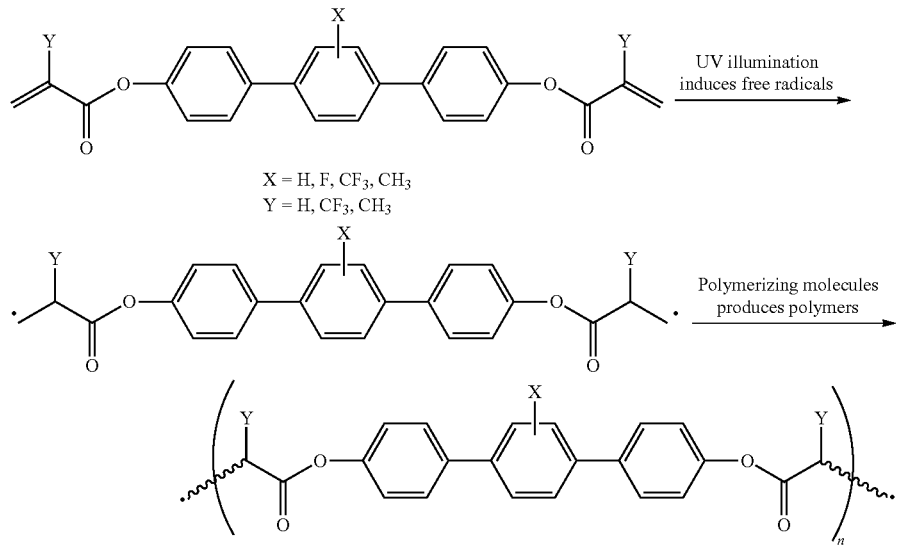

Figure 3:
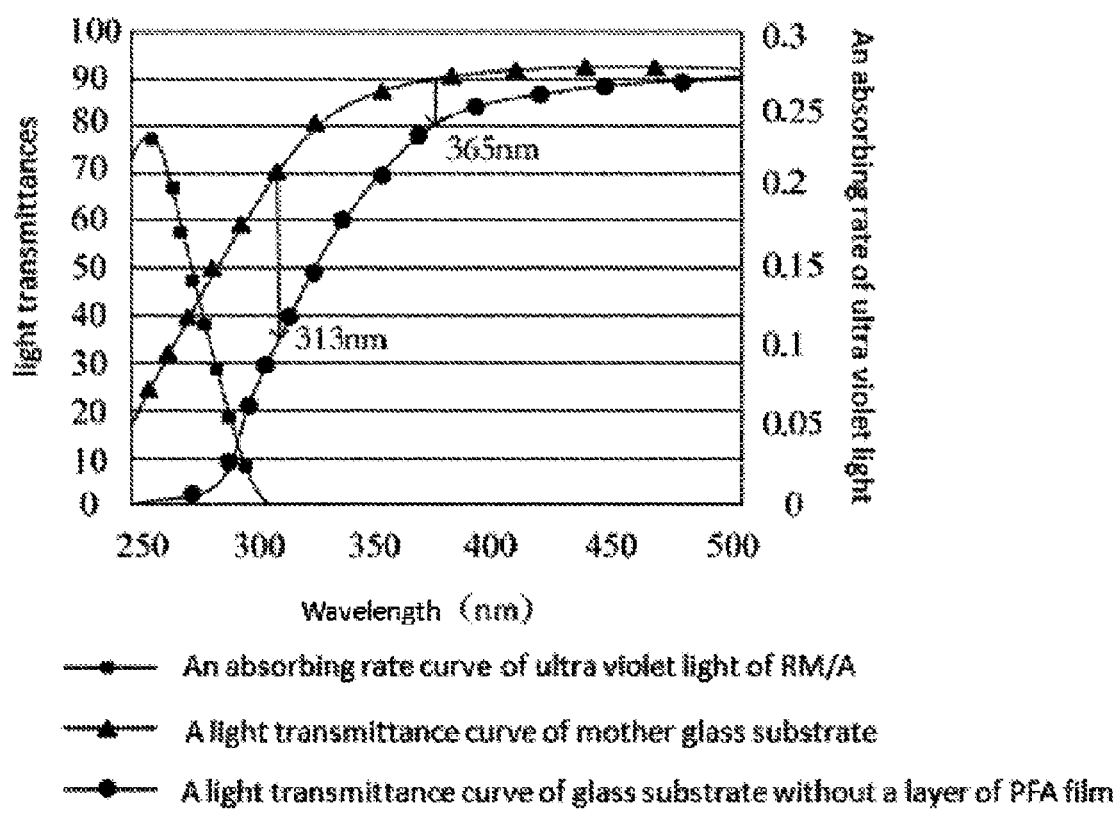
FIG. 3 is a schematic diagram of an absorbing rate of ultra violet light of RM/A changing with wavelengths in the prior art, and a schematic diagram of light transmittances of liquid crystal panels with a layer of PFA film and without a layer of PFA film respectively in glass substrate changing with wavelengths.

Please refer to FIG. 3 and FIG. 4, FIG. 3 is a schematic diagram of an absorbing rate of ultra violet light of RM/A changing with wavelengths in the prior art, and a schematic diagram of light transmittances of liquid crystal panels with a layer of PFA film and without a layer of PFA film respectively in glass substrate changing with wavelengths; FIG. 4 is an effective time and pretilt angel schematic diagram representing a liquid crystal panel without a layer of PFA film at illumination time of 185 s in the prior art, and an effective time and pretilt angel schematic diagram representing a liquid crystal panel with a layer of PFA film in the prior art.

In order to reduce parasitic capacitance and to increase aperture ratio in actual production process, PFA technology usually coats one more layer of organic film on a side with TFT of PV layer, or even completely replace the PV layer, but keep CF side unchanged. PFA is tetrafluoroethylene and Polyfluoroalkoxy resin which can be a organic photoresist material.

However, due to a certain ultra violet light absorbency of PFA, applying PFA on PSVA liquid crystal panel reduces permeability of illumination at TFT side, and then when UV light illuminates from the TFT side with a duration of UV1 unchanged, an insufficient pretilt angel is caused by reducing in ultra violet light absorbency of the reaction monomer of the liquid crystal to effect the optical properties of product. As shown in FIG. 3, a penetration rate of ultra violet wavelength has a larger reduction after coating a layer of PFA on mother glass, the penetration rate reduces 14% at wavelength of 365 nm, and the penetration rate even reduces to 46.25% at wavelength of 313 nm.

TABLE 1

| | Liquid crystal panel | | | |
|---|---|---|---|---|
| | Without PFA | With PFA | | |
| Illumination time(s) | 185 | 185 | 240 | 295 |
| Effeictive time (ms) | 13.1 | 20.7 | 16.3 | 9.4 |
| Pretilt angle (degree) | 88.0 | 88.7 | 88.4 | 87.5 |

From table 1, the best illumination time of UV1 is 185 s in actual production process, but if the illumination time of UV1 keeps unchanged 185 s after adding a layer of PFA, the pretilt angel of the liquid crystal changes from 88.0° to 88.7° and the effective time increases from 13.1 ms to 20.7 ms, so that the effective time of the liquid crystal panel is effected seriously. When the illumination time of UV1 is 240 s, the effective time is 16.3 ms and the pretilt angel is 88.4°, and both of them are still larger than the effective time and the pretilt angel without a layer of PFA. As shown in FIG. 4, when the illumination time of UV1 increases to about 260 s, the effective time and the pretilt angel are consistent to the effective time and the pretilt angel without a layer of PFA and at the illumination time of 185 s, so that the optical properties can match production standard. However, increasing the illumination time from 185 s to 260 s must effect the production of UV1 process and then result into lowering production efficiency.

Figure 5:
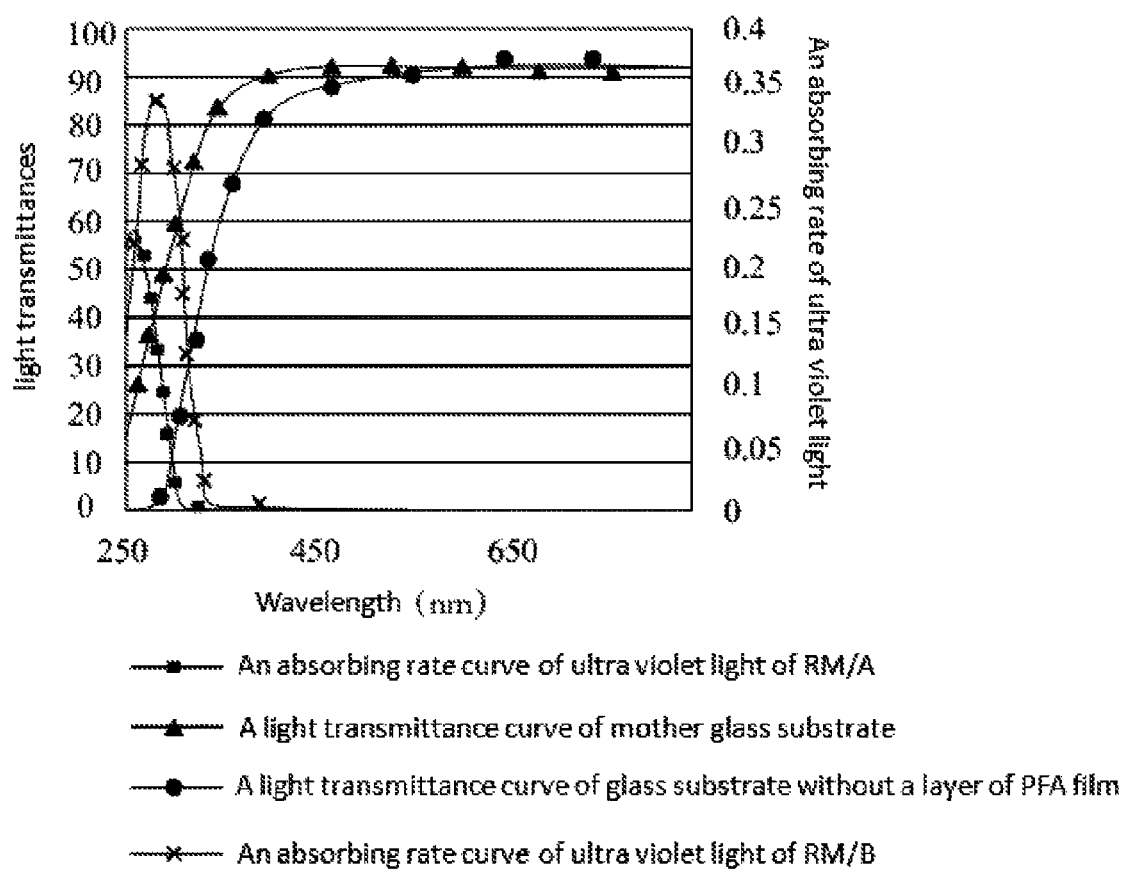
FIG. 5 is a schematic diagram representing absorbing ultra violet rate changing with wavelengths in RM/B of the implementation plan in the liquid crystal panel in the invention and in RM/A in the prior art, and a schematic diagram representing light transmittances changing with wavelengths in a liquid crystal panels without a layer of PFA film in glass substrate and in a liquid crystal panels with a layer of PFA film in glass substrate.
Figure 6:
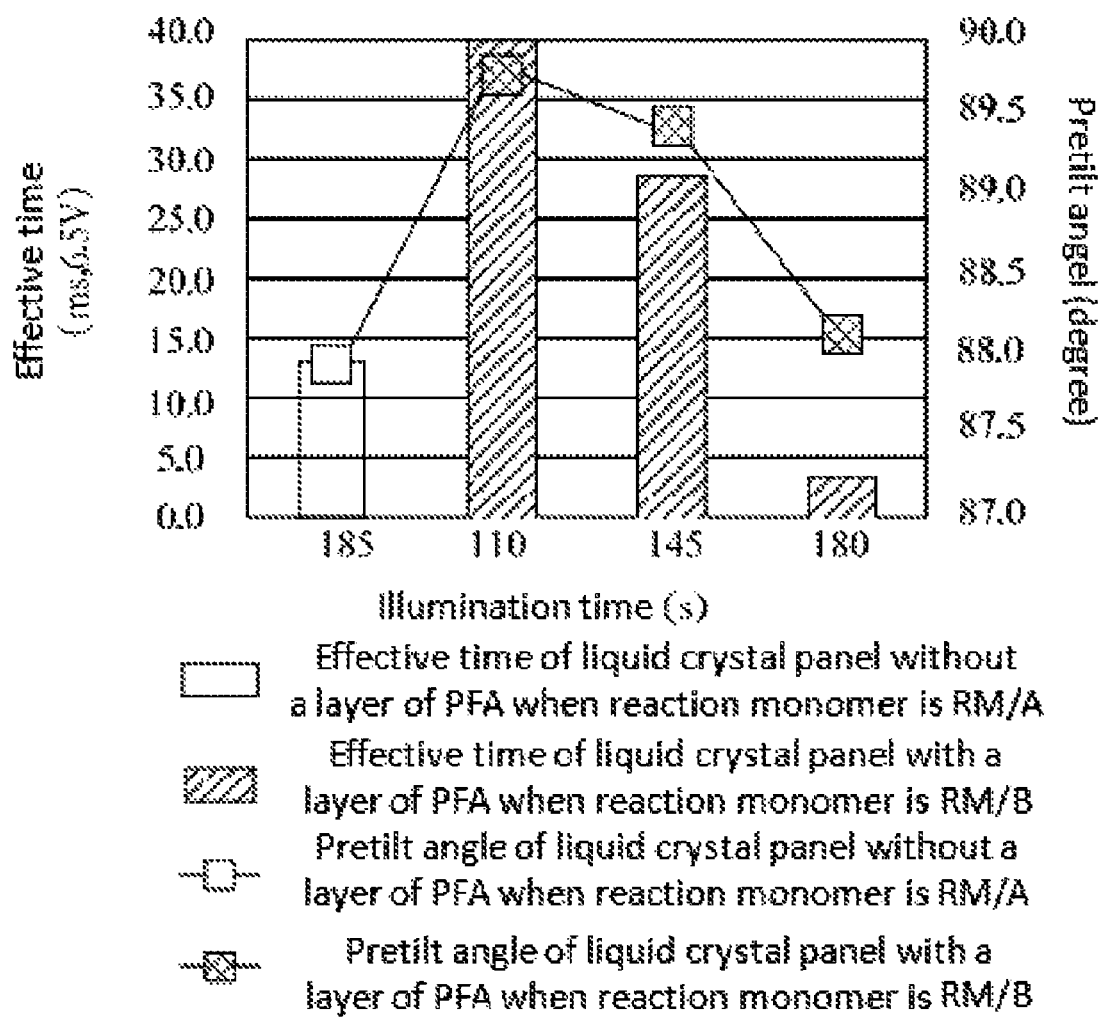
FIG. 6 is a schematic diagram representing an liquid crystal effective time and pretilt angel changing with time in an implementation plan with a layer of PFA film of liquid crystal panel in the invention, and a schematic diagram representing an liquid crystal effective time and pretilt angel at illumination time of 185 s in a liquid crystal panel without a layer of PFA film in the prior art.

Please refer to FIG. 5 and FIG. 6, FIG. 5 is a schematic diagram representing absorbing ultra violet rate changing with wavelengths in RM/B of the implementation plan in the liquid crystal panel in the invention and in RM/A in the prior art, and a schematic diagram representing light transmittances changing with wavelengths in a liquid crystal panels without a layer of PFA film in glass substrate and in a liquid crystal panels with a layer of PFA film in glass substrate; FIG. 6 is a schematic diagram representing an liquid crystal effective time and pretilt angel changing with time in an implementation plan with a layer of PFA film of liquid crystal panel in the invention, and a schematic diagram representing an liquid crystal effective time and pretilt angel at illumination time of 185 s in a liquid crystal panel without a layer of PFA film in the prior art.

As shown in FIG. 5, when the RM/B in the invention replaces the RM/A in the prior art, the ultra violet absorbency is more sufficient. It is shown in the figure that the ultra violet absorbency of RM/A at wavelength of 300 nm is 0.15, but the ultra violet absorbency of RM/B is 0.34, so that the ultra violet absorbency efficiency of RM/B is more effective.

As shown in FIG. 6, when the RM/B in the invention is induced to the PSVA liquid crystal panel with PFA at the illumination time between 145 s-180 s, the effective time can reach to a level of the RM/A without the layer of PFA at UV1 time of 185 s in the prior art.

Table 2 shows when a reactive monomer is RM/B, experimental data of an effective time and pretilt angel of a liquid crystal panel with a layer of PFA at different illumination times, and when a reactive monomer is RM/A, data of a liquid crystal panel without a layer of PFA at illumination time of 185 s.

TABLE 2

| Liquid crystal panel\reactive monomer | | | | |
|---|---|---|---|---|
| | Without PFA\RM/A | withPFA\RM/B | | |
| Illumination time (s) | 185 | 110 | 145 | 180 |
| Effective time (ms) | 13.1 | 152.0 | 28.8 | 3.7 |
| Pretilt angel (degree) | 88.0 | 89.8 | 89.5 | 88.2 |

As shown in table 2, when the reactive monomer is RM/B and the liquid crystal with a layer of PFA at the illumination time of 180 s, the effective time is 3.7 ms and the pretilt angel is 88.2°, and the effective time is far shorter than the effective time of the illumination time of 185 s for the liquid crystal panel with RM/A reactive monomer without a layer of PFA, but a very small difference in pretilt angels.

Furthermore, the invention further provides a electronic equipment, which comprises aforementioned liquid crystal panel.

In summary, after the RM/B in the invention is induced to the PSVA liquid crystal panel with PFA, the ultra violet light absorbency is even more effective and the reactive polymerization of RM/B is faster due to the RM/B in the invention has far plentiful phenyls which is even more sensitive to the ultra violet light, so that a productive effect of PSVA liquid crystal panel from PFA can be recovered, and then production efficiency can be increased. Thus, the implementation plan of liquid crystal panel in the invention can utilized in PSVA liquid crystal panel with PFA without extra manufacturing time cost. Of course, the implementation plan of liquid crystal panel in the invention can utilized in PSVA liquid crystal panel without PFA or in other types of liquid crystal panel.

The above-description is embodiments of the invention only, but not for limiting the patent scope of the invention; therefore, any equivalent structural transformations or equivalent processes utilizing the present invention, or applications applied in other related technical field directly or indirectly are all included in the patent scope of the present invention.

The invention claimed is:

1. A reactive monomer, wherein the reactive monomer comprises a biphenyl structure and polymerizable groups connecting at both sides of the biphenyl structure, a formula of the reactive monomer is shown as formula II:

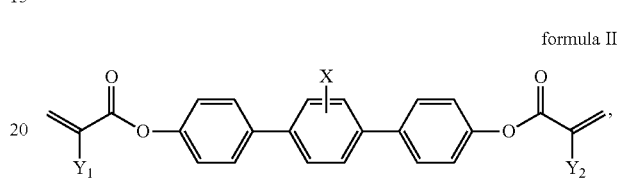

formula II

Wherein, the X is one of $-CF_3$ or $-CH_3$;
the $Y_1$ and $Y_2$ groups are independently $-H$ or $-CH_3$;
a wavelength absorbed by the reactive monomer is 250 nm-400 nm.

2. A liquid crystal panel comprises both a first substrate and a second substrate with disposed alignment films respectively, and a liquid crystal layer disposed between a first substrate and a second substrate, wherein, the liquid crystal layer comprises a liquid crystal compound which comprises at least a reactive monomer; the reactive monomer comprises a biphenyl structure and polymerizable groups connecting at both sides of the biphenyl structure, a formula of the reactive monomer is shown as formula II:

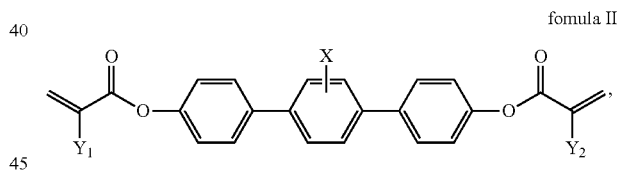

formula II wherein, the X is one of $-CF_3$ or $-CH_3$;
the $Y_1$ and $Y_2$ groups are independently $-H$ or $-CH_3$.

3. The liquid crystal panel according to claim 2, wherein, the first substrate is a color filter substrate; the second substrate is a thin film transistor array substrate; a side of the thin film transistor array substrate further disposes a layer of tetrafluoroethylene and Polyfluoroalkoxy resin film.

4. The liquid crystal panel according to claim 3, wherein, the alignment film is a vertical alignment film.

5. An electronic equipment, wherein the electronic equipment comprises a liquid crystal panel; the liquid crystal panel comprises both a first substrate and a second substrate with disposed alignment films respectively, and a liquid crystal layer disposed between a first substrate and a second substrate, wherein, the liquid crystal layer comprises a liquid crystal compound which comprises at least a reactive monomer; the reactive monomer comprises a biphenyl structure and polymerizable groups connecting at both sides of the biphenyl structure, a formula of the reactive monomer is shown as formula II:

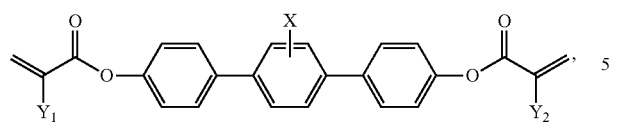

formula II wherein, the X is one of —CF$_3$ or —CH$_3$;
the Y$_1$ and Y$_2$ groups are independently —H or —CH$_3$.

6. The electronic equipment according to claim 5, wherein, the first substrate of the liquid crystal panel is a color filter substrate; the second substrate is a thin film transistor array substrate; a side of the thin film transistor array substrate further disposes a layer of tetrafluoroethylene and Polyfluoroalkoxy resin film.

7. The electronic equipment according to claim 6, wherein, the alignment film is a vertical alignment film.

* * * * *